(12) United States Patent
Allef et al.

(10) Patent No.: US 8,211,841 B2
(45) Date of Patent: Jul. 3, 2012

(54) SKIN AND HAND CLEANSERS

(75) Inventors: Petra Allef, Krefeld (DE); Marcel Veeger, Goch (DE); Markus Hemming, Oberhausen (DE)

(73) Assignee: Evonik Stockhausen GmbH, Krefeld (DE)

( * ) Notice: Subject to any disclaimer, the term of this patent is extended or adjusted under 35 U.S.C. 154(b) by 0 days.

(21) Appl. No.: 12/933,835

(22) PCT Filed: May 13, 2009

(86) PCT No.: PCT/EP2009/055772
§ 371 (c)(1),
(2), (4) Date: Sep. 21, 2010

(87) PCT Pub. No.: WO2009/144139
PCT Pub. Date: Dec. 3, 2009

(65) Prior Publication Data
US 2011/0021398 A1    Jan. 27, 2011

(30) Foreign Application Priority Data

May 30, 2008   (DE) .................. 10 2008 026 051

(51) Int. Cl.
*A61K 8/37*   (2006.01)

(52) U.S. Cl. ........ 510/138; 510/407; 510/425; 510/437; 510/511

(58) Field of Classification Search ................ None
See application file for complete search history.

(56) References Cited

U.S. PATENT DOCUMENTS

| | | | |
|---|---|---|---|
| 4,605,563 A | 8/1986 | Heine et al. | |
| 4,654,220 A | 3/1987 | Heine et al. | |
| 5,444,096 A | 8/1995 | McCrea et al. | |
| 5,597,576 A | 1/1997 | Genova et al. | |
| 5,824,327 A | 10/1998 | Whittemore et al. | |
| 5,891,449 A | 4/1999 | Daniel et al. | |
| 6,235,296 B1 | 5/2001 | Daniel et al. | |
| 6,376,438 B1 | 4/2002 | Rosenberger et al. | |
| 7,241,452 B2 | 7/2007 | Veeger et al. | |
| 7,670,615 B2 | 3/2010 | Veeger et al. | |
| 2004/0170592 A1 | 9/2004 | Veeger et al. | |
| 2005/0031580 A1 | 2/2005 | Allef et al. | |
| 2005/0118124 A1* | 6/2005 | Reinhart et al. | ............... 424/63 |
| 2005/0233914 A1 | 10/2005 | Grascha et al. | |
| 2006/0165627 A1 | 7/2006 | Allef et al. | |
| 2006/0204468 A1 | 9/2006 | Allef et al. | |
| 2007/0041927 A1 | 2/2007 | Blaeser et al. | |
| 2007/0092470 A1 | 4/2007 | Allef et al. | |
| 2008/0145320 A1 | 6/2008 | Wenk et al. | |
| 2008/0227677 A1 | 9/2008 | Grascha et al. | |
| 2008/0305056 A1 | 12/2008 | Jenni et al. | |
| 2009/0054521 A1 | 2/2009 | Herrwerth et al. | |
| 2009/0318570 A1 | 12/2009 | Veeger et al. | |
| 2010/0069505 A1 | 3/2010 | Veeger et al. | |
| 2010/0210499 A1 | 8/2010 | Allef et al. | |

FOREIGN PATENT DOCUMENTS

| | | |
|---|---|---|
| DE | 43 35 933 | 4/1995 |
| EP | 0 141 410 | 5/1985 |
| EP | 0 635 260 | 1/1995 |
| EP | 1 504 081 | 9/2006 |
| WO | 01 85103 | 11/2001 |

OTHER PUBLICATIONS

U.S. Appl. No. 12/446,569, filed Apr. 21, 2009, Veeger, et al.
U.S. Appl. No. 12/674,831, filed Feb. 23, 2010, Wenk, et al.
U.S. Appl. No. 12/863,868, filed Jul. 21, 2010, Allef, et al.

* cited by examiner

*Primary Examiner* — Necholus Ogden, Jr.
(74) *Attorney, Agent, or Firm* — Oblon, Spivak, McClelland, Maier & Neustadt, L.L.P.

(57) ABSTRACT

The invention relates to skin and hand cleansers comprising the components a.) at least one alkyl ester and/or diester, b.) 0 to 40 wt.-% of at least one surfactant selected from the group of fatty alcohol ethoxylates, fatty alcohol ether sulfates and salts of sulfated and/pr sulfonated fatty acids, c.) at least one thixotropic agent and at least one hydrophilic, pyrogenic silicic acid, d.) 0 to 30 wt.-% of one or more abrasives, e.) 0 to 5 wt.-% of at least one physiologically compatible carbonic acid ester f.) 0 to <10 wt.-% water, g.) optionally one or more viscosity modifying agent, h.) optionally other cosmetic aids, additives and/or active ingredients, wherein the total of the components a.) through h.) adds up to 100 wt.-%, based on the composition of the cleanser.

21 Claims, No Drawings

SKIN AND HAND CLEANSERS

The invention relates to skin and hand cleansers which have a low water content or are free from water, in particular for removal of extreme skin contamination.

Skin and hand cleansers are employed extensively in industry, especially where stubborn contamination caused by lacquers, fats, oils, lubricants, metallic dusts, graphite, carbon black and the like arise. Such cleansers are known in particular as so-called heavy duty hand cleansers (cf. H. Tronnier, J. Kresken, K. Jablonski, B. Komp, "Haut and Beruf", Grosse Verlag, Berlin, p. 75-108 [1989]). These are conventionally formulations which comprise an abrasive, surfactant/surfactant mixtures, thickening agents and optionally auxiliary substances for regulating the consistency, appearance, smell and stability, such as pigments, fragrances, stabilizers and preservatives. For particularly stubborn contamination, there are products in which the use of the abovementioned ingredients is not sufficient.

Organic solvents, such as e.g. aliphatic hydrocarbons, terpenes, carboxylic acid esters of the dimethyl adipate, dimethyl glutarate, dimethyl succinate (DBE) and di-n-butyl adipate or di-isopropyl adipate type, such as have been described in DE 43 35 933 A 1, are then added to these formulations.

The so-called "waterless cleaner" obtainable on the market is moreover to be referred to here, the good cleansing action of which being based chiefly on the above-mentioned organic solvents, in particular gasolines, kerosenes, short-chain paraffin oils.

In view of the wide spectrum of use of heavy duty hand cleansers, in particular in the industrial sector, and the fact that skin and hand cleansing contamination when it occurs in this sector can in many cases be particularly stubborn and therefore is usually not accessible to cleansing with conventional skin cleansers, for example in the lacquer processing industry, there continues to be a demand for skin and hand cleansers which show a comparable cleansing action to the products known in the prior art, for example skin and hand cleansers containing DBE. With respect to their cleansing action in the so-called "heavy duty hand cleanser sector", i.e. as compositions for removing extreme contamination, such compositions are to be regarded virtually as standard cleansers with respect to their cleansing action, with the consequence that skin and hand cleansers without DBE as a skin cleansing intensifying component must have an at least qualitatively comparable skin cleansing action in order to find acceptance by the consumer for their intended purpose.

In spite of the abovementioned fact that carboxylic acid esters of the dimethyl adipate, dimethyl glutarate, dimethyl succinate (DBE) and di-n-butyl adipate or di-isopropyl adipate type have an outstanding activity as cleansing intensifiers in skin and hand cleansers, the availability of this cosmetics raw material on the market is limited or often subject to wide variations, which of course has a direct influence on the production costs of the end products. It has moreover been found that skin and hand cleanser formulations which contain DBE as a cleansing intensifier often additionally have to be stabilized in order to obtain marketable products. This is associated with an additional burden of costs on the end products. It would therefore be advantageous to be able to employ both skin and hand cleanser formulations which contain DBE as the skin cleansing intensifying component and are stabilized in a simple manner, as well as skin and hand cleanser formulations stabilized in the same manner which contain an alternative to the abovementioned carboxylic acid esters of the DBE type as cleansing power intensifiers.

Thus, for example, EP 1 504 081 B1 describes skin and hand cleansers based on fatty acid methyl esters. A disadvantage of the skin and hand cleansers described in this document is that these skin and hand cleansers contain 10 to 80 wt. % of water. This not only leads to a reduced cleansing performance, but there is the risk of hydrolysis and increased oxidation, in particular of the methyl esters in these aqueous formulations, which is accompanied by a reduction in the storage stability of such skin and hand cleansers.

Attempts aimed at preparing formulations of low water content, i.e. formulations having a water content of <10 wt. %, starting from EP 1 504 081 B1 led to unstable products, or the products obtained formed no flow limit in order to prevent abrasive particles optionally employed in the skin and hand cleanser from settling in the formulation, i.e. stable incorporation of abrasive particles is made distinctly difficult or is impossible.

The object was therefore to provide skin and also hand cleansers which have a low water content or are free from water, in particular for cleansing from extreme skin and hand cleansing contamination with a water content of <10 wt. %, based on the total products, which, with the formation of a flow limit in order to prevent abrasive particles optionally employed in the skin and hand cleanser from settling in the formulation, not only have a comparable cleansing action to those which are commercially obtainable, but are also simple to prepare in production terms, and these skin and hand cleansers should have a flash point of >100° C. and a vapor pressure at 20° C. of >0.01 hPa, the skin and hand cleansers being stabilized in a simple manner such that they have a good storage stability as homogeneous and stable end products.

The object was achieved, surprisingly, by a skin and hand cleanser which is free from water or has a low water content and comprises the components a.) at least one alkyl ester and/or diester b.) 0 to 40 wt. % of at least one surfactant chosen from the group of fatty alcohol ethoxylates, fatty alcohol ether sulfates and salts of sulfated and/or sulfonated fatty acids, c.) at least one thixotropy agent and at least one hydrophilic, pyrogenic silica, d.) 0 to 30 wt. % of one or more abrasives, e.) 0 to 5 wt. % of at least one physiologically acceptable carbonic acid ester f.) 0 to <10 wt. % of water, g.) optionally one or more viscosity-forming agents, h.) optionally further cosmetics auxiliary substances, additives and/or active compounds, the sum of components a.) to h.) being 100 wt. %, based on the composition of the cleanser.

It was completely surprising that stable and storage-stable skin and hand cleansers based on fatty acid alkyl esters and having a water content of <10 wt. %, based on the total composition, can be obtained if these compositions contain a synergistic combination of at least one thixotropy agent with at least one hydrophilic, pyrogenic silica as a component.

The alkyl esters of component a.) which are to be employed according to the invention can be fatty acid alkyl esters prepared synthetically, for example obtained as reaction products of fatty acids with lower aliphatic alcohols, or alternatively also by the route of transesterification of natural or synthetic fats and oils, where in the case of fatty acid alkyl esters which originate from naturally occurring oils, these are appropriately processed or purified industrially for cosmetics use. Fatty acid alkyl esters of component a.) have, for example, the general formula (I), namely $$R^1CO-OR^2 \tag{I}$$

in which $R^1CO$ represents a linear or branched, saturated and/or unsaturated acyl radical having 6 to 22, in particular 8 to 22, preferably 12 to 22 carbon atoms and $R^2$ represents an alkyl radical having 1 to 8 carbon atoms, in particular an alkyl radical having 1 to 4 carbon atoms, and particularly preferably a methyl radical.

Preferred synthetic fatty acid alkyl esters here are, for example, synthetic methyl, ethyl, propyl, isopropyl esters, n-butyl, isobutyl, tert-butyl and the corresponding pentyl and hexyl esters, in particular also fatty acid 2-ethylhexyl esters, Fatty acid methyl esters, fatty acid isopropyl esters and fatty acid 2-ethylhexyl esters which are preferred according to the invention are obtainable from Cognis under the trade name TEXAPRINT®.

Further typical examples are the methyl, ethyl, propyl or butyl esters of caproic acid, caprylic acid, capric acid, lauric acid, myristic acid, palmitic acid, palmoleic acid, stearic acid, isostearic acid, oleic acid, elaidic acid, linoleic acid, linolenic acid, gadoleic acid, arachidonic acid, behenic acid and erucic acid and technical grade mixtures thereof.

In particular, those fatty acid esters which can be derived from so-called plant oils are also employed according to the invention, namely the plant oil esters obtainable by esterification of, for example, soya, sunflower, coconut or rapeseed oil with an alcohol. The fatty acid methyl esters which can be obtained, for example, under the name Edenor ME SU likewise from Cognis are particularly preferred as component a.) here.

The alkyl esters of component a.) can furthermore be diesters, such as, for example, dimethyl adipate, dimethyl glutarate, dimethyl succinate (DBE), di-n-butyl adipate, di-isopropyl adipate or dimethyl 2-methyl-glutarate. They have, for example, the general formula (II), namely

$$R^1OOC-X-COOR^2 \quad (II)$$

in which X represents a linear or branched, saturated and/or unsaturated alkyl radical having 0 to 20, preferably 0 to 6 carbon atoms and $R^1$ and $R^2$ represents an alkyl radical having 1 to 8 carbon atoms, in particular a methyl radical.

The alkyl esters and/or diesters of component a.) can be employed by themselves or as mixtures, the methyl esters being particularly preferred.

The skin and hand cleansers according to the invention preferably contain 5 to 90 wt. %, based on the total composition, preferably 10 to 65 wt. % and particularly preferably 25 to 65 wt. % of alkyl esters and/or diesters of component a.).

The fatty alcohol ethoxylates which can be employed as component b.) preferably have the general formula

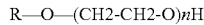

$$R-O-(CH2-CH2-O)nH$$

wherein
R=saturated, unsaturated, branched or unbranched alkyl radical,
n=integer from 1 to 11.

Preferably, $R=C_6$ to $C_{18}$, in particular $C_{10}$ to $C_{16}$ and particularly preferably $C_{11}$ to $C_{14}$ are used as the saturated, unsaturated, branched or unbranched alkyl radical, where preferably n=3 to 6, in particular n=5 to 7.

The fatty alcohol ether sulfates of component b) which can be chosen are in particular those of the general formula

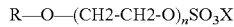

$$R-O-(CH2-CH2-O)_nSO_3X$$

where R=a $C_8$-$C_{18}$, preferably $C_{11}$-$C_{14}$ saturated or unsaturated, branched or unbranched alkyl radical, n=an integer from 1 to 6, preferably 1 to 4, and $X=Na^+$, $NH_4^+$ or $Mg^{2+}$, sodium lauryl ether sulfate (where $R=C_{12}$, n=2-3 and $X=Na^+$) being particularly preferred.

Salts of sulfated and/or sulfonated fatty acids of component b.) which are used according to the invention are alkali metal or alkaline earth metal salts of $C_8$-$C_{30}$, preferably $C_{10}$-$C_{22}$ fatty acids, particularly preferably castor oil sulfates, in particular $Na^+$ or $NH_4^+$ sulfates. Such castor oil sulfonates are obtainable, for example, under the to brands Monobrilliantöl® (Evonik Stockhausen GmbH, Krefeld) or Standapol SCO® (Cognis Deutschland GmbH & Co.KG, Düsseldorf).

The skin and hand cleansers according to the invention preferably contain 1 to 40 wt. %, preferably 5 to 30 and particularly preferably 10 to 30 wt. % of component b), preferably fatty alcohol ethoxylates, based on the composition of the cleanser. In a preferred embodiment, the skin and hand cleansers according to the invention contain 5 to 35 wt. %, based on the composition of the cleanser, of laureth-6 as a fatty alcohol ethoxylate.

It is essential to the invention that the skin and hand cleansers according to the invention necessarily contain component c.), namely a combination comprising at least one thixotropy agent and at least one hydrophilic, pyrogenic silica.

According to the invention, a thixotropy agent is understood as meaning an agent which is suitable for increasing the flow limit of a disperse system, such as e.g. a cosmetics formulation containing abrasive. Such thixotropy agents are known, for example, as "rheological additives" for a large number of uses, in particular for the preparation of lacquers and paints, where they act as so-called "antisettling agents". These are, for example, bentonites, kaolins, alginic acid, but also the industrially important $SiO_2$ modifications, such as e.g. silica earth and kieselguhr as well as silica gels.

In cosmetics formulations, such thixotropy agents are also responsible for the formation of a solid so-called "house of cards gel structure". This applies in particular to cosmetics formulations which contain polar organic media. However, such a "house of cards structure" does not form in skin and hand cleansers which contain ethoxylated fatty alcohols as cleansing intensifiers, or this structure is so greatly disturbed that stabilization of such a cosmetics formulation is no longer ensured.

It has now been found, surprisingly, that such systems can be stabilized if these cosmetics formulations, in particular skin and hand cleansers, contain a hydrophilic, pyrogenic silica alongside a thixotropy agent.

Hydrophilic, pyrogenic silicas are highly disperse silicas, i.e. $SiO_2$ modifications which have been prepared by flame hydrolysis, it being possible for the surfaces of such pyrogenic silicas to be subjected to a chemical after-treatment, so that the spectrum of silicas obtainable is extended by this means and silicas with hydrophobized surfaces can also be obtained. The hydrophilic, pyrogenic silicas of component c.) which are to be employed according to the invention are obtainable, for example, under the trade name AEROSIL®.

The skin and hand cleansers according to the invention contain >0.1% wt. % of a hydrophilic, pyrogenic silica, in particular 0.5 to 5.0 wt. %, based on the total composition of the formulation, hydrophilic, pyrogenic silicas which are obtainable under the trade name AEROSIL® 200 being particularly preferred.

The skin and hand cleansers according to the invention contain thixotropy agents of component c.) to the extent of 0.5 to 10 wt. %, based on the total composition, preferably 0.5 to 7.5 and particularly preferably 2 to 6 wt. %. Preferred thixotropy agents are organophilic and/or hydrophobic laminar silicates, in particular bentonites, preferably in which the inorganic cations of natural bentonites, e.g. Na bentonite, are replaced by organic radicals, in particular quaternary ammonium cations, such as, for example, in the bentonites marketed by Rockwood Clay Additives, Moosburg, Germany under the trade name TIXOGEL®.

Such organic bentonites can be characterized, for example, via determination of their loss on ignition at 1,000° C., which can be regarded as a conclusive parameter for the ratio of organic radical/bentonites ratio. The loss on ignition here includes the total organic content of the bentonite and the chemically bonded water of the bentonite (approx. 8% in the case of pure bentonite).

It has now been found that bentonites which show a loss on ignition of max. 30% in combination with a hydrophilic, pyrogenic silica ensure an adequate stability in a water-free, solvent-based skin and hand cleanser, so the product instabilities were no longer to be found.

Stearalkonium bentonites, according to INCI nomenclature here, with a loss on ignition of max. 29%, such as e.g. stearalkonium bentonites which can be obtained under the trade name TIXOGEL® LG-M from Rockwood Clay Additives GmbH, Moosburg, Germany and show a loss on ignition of approx. 28%, are particularly preferred according to the invention. The skin and hand cleansers according to the invention preferably contain such stearalkonium bentonites in an amount of >0.5 wt. %, based on the total composition, and particularly preferably >2 wt. %.

It was surprising that such stearalkonium bentonites which show a loss on ignition of max. 29%, such as e.g. the stearalkonium bentonites obtainable under the trade name TIXOGEL® LG-M, and have hitherto be used in particular in nail varnishes for stabilizing colored pigments, can now also be employed for stabilizing cosmetics formulations which are free from water or have a low water content, in particular for skin and hand cleansers.

The skin and hand cleansers according to the invention show a very good cleansing action, but nevertheless the skin and hand cleansers can optionally contain abrasives as an optional component d.) for certain cleansing uses. The content of the abrasive or abrasives can then be 0 to 30 wt. %, based on the composition of the cleanser, preferably 5 to 30 wt. %, particularly preferably 5 to 25 wt. %. In addition to abrasive substances, such as e.g. sand, pumice flour, calcium carbonate and kaolin, abrasives which are preferably to be used are, for example, abrasives of plastic based on polyethylene or polyurethane, abrasives based on natural kernel, husk and/or shell flours, in particular walnut shell, almond shell, hazelnut shell, olive kernel, apricot kernel and cherry kernel and maize flour or any desired mixtures of these shell and kernel flours and beads of waxes, such as e.g. jojoba waxes. walnut shell flour bleached with hydrogen peroxide being particularly preferred.

In a particularly preferred embodiment of the invention, the skin and hand cleansers according to the invention contain as abrasives water-swellable solid particles of organic polymers of natural and/or synthetic origin which, as well as acting as cleansing intensifiers, prevent coagulation and redeposition of the dissolved or emulsified dirt when the compositions are used.

Such water-insoluble, rather merely water-swellable solid particles of organic polymers of natural and/or synthetic origin as abrasives for skin and hand cleansers are described, for example, in DE 37 36 970. These are polymers based on modified natural substances or based on synthetic products, water insolubility thereof in general being achieved by crosslinking. The term polymers in this context includes both the homo- and the co- and terpolymers.

Suitable organic polymers based on modified natural substances are, for example, the products based on starch and cellulose, which can be modified by grafting, preferably with acrylic derivatives. Such acrylic derivatives are, for example, (meth)acrylic acid and salts thereof, (meth)acrylonitrile, (meth)acrylamide and the (meth)acrylic esters, and the partial saponification products of these acrylic derivatives.

Synthetic organic polymers which are to be mentioned are the homo- and copolymers, in particular of the abovementioned acrylic derivatives. These are essentially crosslinked polyacrylic acids or crosslinked starch/acrylic acid graft copolymers in which the carboxyl groups can be partially neutralized with sodium or potassium ions. The polymers can contain as comonomers acrylamidopropanesulfonic acid, vinylphosphonic acid, vinylsulfonic acid, dialkylaminoalkyl (meth)acrylates, dialkylamino(meth)acrylamides and the quaternized forms of the two above-mentioned basic comonomers. Polyurethanes are furthermore also suitable.

Abrasives which are preferred according to the invention are those in the form of water-swellable polymers which are obtainable by polymerization of the components aa.) 55 to 99.95 wt. % of monoethylenically unsaturated monomers which carry carboxyl groups,
bb.) 0.05 to 5.0 wt. % of at least one crosslinking agent,
cc.) 0 to 40 wt. % of further monomers which can be copolymerized with a.),
dd.) 0 to 30 wt. % of a water-soluble graft base, and the constituents aa.) to dd.) add up to 100 wt. %, it being possible for the polymers obtained optionally to be post-crosslinked at least once.

Monoethylenically unsaturated monomers of component aa.) which carry carboxyl groups and which are to be mentioned here are, in particular, monoethylenically unsaturated $C_3$ to $C_{1-10}$-monocarboxylic acids and alkali metal and/or ammonium and/or amine salts thereof. These monomers include, for example, acrylic acid, methacrylic acid, dimethacrylic acid, ethylacrylic acid, crotonic acid, isocrotonic acid, vinylacetic acid and allylacetic acid. From this group, acrylic acid, methacrylic acid or alkali metal or ammonium salts thereof or mixtures thereof are used as preferred monomers, acrylic acid and sodium, potassium or ammonium salts thereof being particularly preferred as monomers.

Further monoethylenically unsaturated monomers which carry carboxyl groups are also the monoethylenically unsaturated $C_4$ to $C_8$-dicarboxylic acids, anhydrides thereof and alkali metal and/or ammonium and/or amine salts thereof. Suitable dicarboxylic acids are, for example, maleic acid, fumaric acid, itaconic acid and methylenemalonic acid, maleic acid, maleic anhydride, itaconic acid, itaconic anhydride and the corresponding sodium, potassium or ammonium salts of maleic or itaconic acid being preferred.

Monoethylenically unsaturated monomers which carry carboxylic groups are also the hydrolysis products of (meth)acrylonitrile copolymers and of starch/(meth)acrylonitrile graft copolymers, hydrolysis products of (meth)acrylamide copolymers and saponification products of (meth)acrylic acid copolymers with ethylenically unsaturated esters as a polymer containing carboxylate groups.

The acid, polymerized-in monomer constituents of the water-swellable polymers are preferably neutralized at least to the extent of 25 mol % and preferably to the extent of at least 50 mol % and particularly preferably to the extent of at least 75 mol % and, as described above, are present for example as the sodium, potassium or ammonium salt or mixtures thereof.

Compounds which have at least two ethylenically unsaturated double bonds or an ethylenically unsaturated double bond and a functional group which is reactive towards acid groups or several functional groups which are reactive towards acid groups are conventionally employed as crosslinking agents of component bb.). Preferred crosslinking agents are those which contain at least two ethylenically unsaturated double bonds, such as e.g. methylenebisacrylamide or -methacrylamide or ethylenebisacrylamide, furthermore esters of unsaturated mono- or polycarboxylic acids of polyols, such as diacrylates or triacrylates, e.g. butanediol diacrylate or -methacrylate or ethylene glycol diacrylate or -methacrylate, trimethylolpropane triacrylate, and alkoxylates thereof with preferably 1 to 30 mol of ethylene oxide, furthermore allyl compounds and alkoxylates thereof, such as allyl(meth)acrylate, allyl $(EO)_{1-30}$(meth)acrylate, triallyl cyanurate, maleic acid diallyl ester, polyallyl esters, tetraallyloxyethane, di- and triallylamine, tetraallylethylenediamine, allyl esters of phosphoric acid or of phosphorous acid.

Compounds which have at least one functional group which is reactive towards acid groups and are to be mentioned here are, for example, the N-methylol compounds of amides, such as e.g. methacrylamide or acrylamide and the ethers derived therefrom, but also di- and polyglycidyl compounds.

The crosslinking agents can be employed by themselves or in combination in amounts of from 0.05 to 5.0 wt. %, preferably to the extent of 0.05 to 2.0 wt. % and particularly preferably to the extent of 0.1 to 1.0 wt. %, based on the monomers.

In addition to the monoethylenically unsaturated monomers which carry carboxyl groups and the crosslinking agent (components aa.) and bb.)), further comonomers for modification of the properties which are substantially soluble in an aqueous monomer solution can optionally be present as component cc.) in the preparation of these water-swellable polymers. Such comonomers can be, for example, (meth)acrylamide, (meth)acrylonitrile, vinylpyrrolidone, vinylacetamide, 2-acrylamido-2-methylpropanesulfonic acid, vinylsulfonic acid, (meth)allylsulfonic acid, hydroxyethyl acrylate, alkyl polyethylene glycol (meth)acrylates, alkylaminoalkyl(meth)acrylates, alkylaminopropylacrylamides, acrylamidopropyltrimethylammonium chloride or mixtures thereof. Such comonomers should not exceed a content of 40 wt. %, since they may impair, where appropriate, the swellability of the resulting water-swellable polymer.

The water-swellable polymers can moreover contain water-soluble polymers as component dd.) as a graft base, which are optionally present in amounts of up to 30 wt. %. These include, inter alia, partially or completely saponified polyvinyl alcohols, polyacrylic acids, polyglycols or mixtures thereof, polysaccharides, such as e.g. starch or starch derivatives, cellulose or cellulose derivatives, and also polycarboxypolysaccharides. The latter are either derived from polysaccharides which naturally contain no carboxyl groups and are provided with carboxyl groups by subsequent modification, or they naturally already contain carboxyl groups and are optionally subsequently provided with further carboxyl groups by modification.

The first group of polysaccharides includes, for example, starch, amylose, amylopectin, cellulose and polygalactomannans, such as guar and carob bean flour, and the second group includes e.g. xanthans, alginates, gum arabic etc.

As already mentioned, the carboxyl groups either are naturally present due to the given molecular structure, for example due to uronic acid units in the polysaccharide molecule, or are incorporated by subsequent modification with reagents containing carboxyl groups or are produced by oxidation reactions. Among the polycarboxypolysaccharides into which the carboxyl groups can be incorporated by subsequent modification, carboxyalkyl derivatives are preferred, in particular the carboxymethyl derivatives. Among the polycarboxypolysaccharides in which the carboxyl groups are produced by oxidation of the polysaccharide molecule, oxidized starches and derivatives thereof are preferred in particular.

As well as having carboxyl groups, polycarboxypolysaccharides can be modified with further groups, in particular those which improve the water-solubility, for example hydroxyalkyl, in particular hydroxyethyl groups, and phosphate groups.

Particularly preferred polycarboxypolysaccharides are carboxymethyl-guar, carboxylated hydroxyethyl- or hydroxypropylcellulose, carboxymethylcellulose and carboxymethyl-starch, oxidized starch, carboxylated phosphate starch, xanthan and mixtures of the individual polycarboxypolysaccharides. Carboxymethylcellulose is preferably employed in particular.

Polycarboxypolysaccharide derivatives with low and high degrees of carboxyl substitution can be employed. However, they conventionally have an average degree of carboxyl substitution in the range of from 0.3 to 1.5, polycarboxypolysaccharide derivatives having a degree of substitution in the range of from 0.4 to 1.2 preferably being employed.

With respect to component dd.), it is also to be noted that the molecular weights of the polymers added as the graft base must be adapted to the circumstances of the polymerization conditions. Thus e.g. in the case of an aqueous solution polymerization, it may be necessary to employ only low or medium molecular weight polymers, whereas this factor plays only a minor role in the case of suspension polymerization.

It is furthermore known that the profile of properties of water-swellable polymers can be improved by the process of subsequent surface crosslinking. During such post-crosslinking, the carboxyl groups of the polymer molecules on the surface of the water-swellable polymer particles are crosslinked with crosslinking agents at elevated temperature. Post-crosslinking agents which are employed are compounds which have at least two functional groups and which can crosslink the functional groups of the polymer on the surface of the polymer particles. In this context, alcohol, amine, aldehyde, glycidyl, epichloro and isocyanate functions are preferred, it also being possible to employ crosslinker molecules with several different functions, but also polyvalent metal salt compounds. Typical examples of post-crosslinking agents are: ethylene glycol, diethylene glycol, triethylene glycol, glycerol, polyglycerol, propylene glycol, diethanolamine, triethanolamine, sorbitan fatty acid esters, trimethylolpropane, pentaerythritol, polyvinyl alcol, sorbitol, ethylene carbonate, proypylene carbonate, polyepoxides, such as e.g. ethylene glycol diglycidyl ether, aziridines and polyisocyanates. Ethylene carbonate is preferably used as the post-crosslinking agent. The post-crosslinking agents are employed in an amount of from 0.01 to 10 wt. %, preferably 0.1 to 5 wt. %, particularly preferably 0.1 to 1.5 wt. %, based on the polymer to be post-crosslinked, it being possible for the subsequent surface crosslinking optionally to be repeated several times.

Monomers which carry carboxyl groups and can be employed in the preparation of the water-swellable polymers which contain carboxylate groups and are to be used according to the invention are, for example, acrylic acid, methacrylic acid, vinylacetic acid, maleic acid and mixtures thereof. The use of acrylic acid by itself or mixtures thereof is preferred.

In addition to polymers which are obtained by crosslinking polymerization of partially neutralized acrylic acid, those which additionally contain contents of graft-polymerized starch and/or polyvinyl alcohol can also be used.

The skin and hand cleansers according to the invention can contain up to 30 wt. %, based on the total composition of the skin and hand cleanser, preferably 1 to 25 wt. %, particularly preferably 1 to 15 wt. % of such water-swellable solid particles which act as abrasives, by themselves or with one or more of the abovementioned cosmetics abrasives.

Water-swellable abrasives which are preferred according to the invention are those which are obtainable from Evonik Stockhausen, Krefeld (Germany) under the trade name Favor® T 5056 F. Water-swellable polymers acting as abrasives and bleached walnut shell flour, which can likewise be obtained from Evonik Stockhausen under the name ASTOPON®, are particularly preferred as component d).

The skin and hand cleansers according to the invention can furthermore optionally contain as component e.) 0 to 5 wt. %, preferably 0.5 to 2.5 wt. % of at least one physiologically acceptable carbonic acid ester, i.e. a carbonic acid ester which is acceptable for cosmetics uses, preferably propylene carbonate.

In the case of water-free skin and hand cleanser formulations or the use of stearalkonium bentonites with a loss on ignition of max. 30% as the thixotropy agent, such carbonic acid esters, such as e.g. propylene carbonate, not only act as activating agents, but have the effect in the formulations according to the invention, in addition to stabilization of the recipe, in particular at room temperature (20° C.) and during cold storage (4° C.), also of an antisettling action, which it was not possible to achieve by other stearalkonium bentonites with a loss on ignition of >30%.

The skin and hand cleansers according to the invention are preferably free from water or have a low water content or contain only 0 to <10 wt. % as component f.).

The skin and hand cleansers according to the invention can moreover optionally one or more viscosity-forming agents as component g.), such as, for example, polysaccharides, such as e.g. cellulose, guar flour and/or xanthans, modified polysaccharides, preferably cellulose ethers, carboxyalkylcellulose and/or hydroxyalkylcelluloses, preferably hydroxyethylcellulose, and/or inorganic electrolytes, preferably sodium chloride and/or magnesium sulfate.

The skin and hand cleansers according to the invention can furthermore optionally contain further cosmetics auxiliary substances, additives and/or active compounds, for example pH regulators, stabilizers, preferably cetearyl alcohol and/or hydrogenated castor oils, such as e.g. trihydroxystearin, fragrances, preservatives, preferably organic acids and antioxidants, such as e.g. vitamin E acetate, as component h.). Oily or aqueous care components, such as e.g. bisabolol, aloe vera, panthenol, sodium PCA, jojoba oil, creatin etc., can preferably also be employed in order to emphasize the care action. The same applies to the optional additional use of care components, such as hydrophilic emollients, such as e.g. partial glycerides or oils, by means of which a significantly increased skin care action can be observed, or a very good care effects are with polyglyceryl partial esters, such as have been described in DE 10 2007 022 693. Conventional cosmetics super- or re-oiling agents, such as e.g. isooctyl stearates, can furthermore also be employed in order to minimize the drying-out effects on the skin, in particular due to the use of the solvents employed.

The additional use of hydrogenated castor oil, such as e.g. RHEOCIN® (Rockwood Clay Additives, Moosburg, Germany) or also other waxes as stabilizing agents, preferably 0.5 to 5 wt. %, particularly preferably 0.5 to 3 wt. %, based on the total composition of the cleanser, is particularly advantageous, where appropriate, in particular in order not only to achieve a stabilizing at different storage temperatures, but also to achieve the necessary heat stability of the cosmetics formulations, in particular at 40° C.

In this connection, it is to be emphasized that stable and storage-stable skin and hand cleansers based on alkyl esters and having a water content of <10 wt. %, based on the total composition, can only be obtained if these compositions contain, according to the invention, a synergistic combination of at least one thixotropic agent with at least one hydrophilic, pyrogenic silica as a component. Cosmetics formulations with stearalkonium bentonite and hydrogenated castor oil were not able to stabilize the total system adequately. Only by the addition according to the invention of a hydrophilic silica, such as e.g. AEROSIL 200, was it possible to realize an adequate stabilization, in particular at room temperature.

The skin and hand cleansers, in particular heavy duty cleansers, according to the invention are conventionally prepared by means of known devices in a batch or continuous process, the skin and hand cleansers preferably being obtained as creamy compositions or as flowable viscous pastes. Suitable devices are heatable tanks with a stirrer, continuous mixers, such as extruders, and dispersing apparatuses.

The skin and hand cleansers according to the invention can be used, for example, by first distributing the cleanser on the skin, preferably without water, and then wiping it off with a cloth, preferably a disposable article of paper, plastic or textile fabric etc., without water. However, use with the aid of water is also possible. In this case the product is rinsed off together with the contamination.

The skin and hand cleansers according to the invention are employed for removal of heavy duty contamination which adheres firmly to the skin, such as, for example, fats, oils and other lubricants, paints, lacquers, tar, graphite, carbon black, colored pigments and similar substances such as occur in the industrial and public sector, in manual work, in agriculture and also in the home. The skin and hand cleansers according to the invention are particularly advantageous in the cleansing from the most stubborn lacquer contamination, where the cleanser should contain at least 10 wt. %, based on the composition, of fatty alcohol ethoxylates in this case.

Particularly preferred skin and hand cleansers are free from water and contain at least 10 wt. % of the corresponding methyl esters of the alkyl esters and/or diesters according to the invention as component a.) and at least 5 wt. % of fatty alcohol ethoxylate as component b.), preferably laureth-6.

The invention is described by the following examples and investigations, such as skin tolerability testing with the aid of the Duhring chamber test, drying out of the skin with the aid of a corneometer and cleansing power with the aid of the hand washing test.

Test Methods

Stability Testing

The stability testing was carried out in accordance with the IFSCC Monograph 1992 Number 2 "The Fundamentals of Stability Testing". Chapter IV page 8 there describes standard test conditions, which served as the basis for the stability tests carried out. The standard test conditions in chapter IV.i.a were used at 4° C., RT and 40° C. over a period of 3 months.

Testing the Cleansing Power with the Aid of the Hand Washing Test

The test model of the hand washing test with lacquer provides information on the cleansing action of the products to be tested. For relevance in practice, it is necessary for all the volunteers to have a characteristic skin structure of the palms caused by manual work. The following test was performed with in each case one product in the morning and afternoon.
Test Procedure with Water:
- 0.5 g of dirt (lacquer) is spread and rubbed on the palm and on the back of the hand
- allow to dry for 1½ min
- 1.2 g of cleanser are applied and rubbed in
- 1 ml of water is added and the hands are washed for 30 s
- add another 1 ml of water and wash for 30 s
- rinse off under running cold water
- visual evaluation of the residual contamination (RC) on the back of the hand and the palm according to the scale below 0=clean 5=no cleansing effect (graduation in steps of 0.5 possible)

The percentage cleansing effect is calculated according to the following formula:

$$\text{Cleansing effect } [\%] = \frac{10 - (\overline{RC}_{inside} + \overline{RC}_{outside})}{10} * 100\%$$

$\overline{RC}_{inside}$=mean of the residual contamination on palms of n measurement series (volunteers)
$\overline{RC}_{outside}$=mean of the residual contamination on outsides of hands of n measurement series (volunteers)

Since the determination of the cleansing action has a relatively high range of variation as a result of the test method, an absolute deviation of 5% between two measurement series is permitted.

A good cleansing action is achieved when the cleansing effect is at least 90%. At lower percentage values, significant residual contamination is already seen in the cleansing of hands.

Lacquer Employed:
Zero Glanzcolor Buntlack

EMBODIMENT EXAMPLES

Skin and hand cleansers according to the compositions stated in Tables 1 and 2 were prepared by homogeneous dispersion of all the components at room temperature, during which it is to be ensured that the organic gelling agent obtainable under the name RHEOCIN® from Rockwood Clay Additives, Moosburg, Germany is incorporated into the formulation at a temperature of at least 40° C.

The compositions were characterized with respect to their cleansing action on a lacquer and with respect to their stability.

As shown in the following Tables 1, 2 and 3, skin and hand cleansers according to the invention have, for example, the following compositions:

TABLE 1

| | All recipe examples in wt. %. | | | | | | | | | |
|---|---|---|---|---|---|---|---|---|---|---|
| | 1 | 2 | 3 | 4 | 5 | 6 | 7 | 8 | 9 | 10 |
| Fatty acid alkyl ester from C6, in particular plant oil ester, such as e.g. rapeseed methyl ester or soya fatty acid methyl ester | 54.60 | 50.50 | 50.50 | 50.50 | 50.50 | 64.60 | 11.00 | 40.00 | 48.00 | 47.50 |
| Fatty alcohol ethoxylate (e.g. Rewopal LA6) | 15.00 | 19.50 | 19.50 | 19.50 | 19.50 | 10.00 | 5.00 | 30.00 | 20.00 | 20.00 |
| Stearalkonium bentonite (e.g. TIXOGEL LG-M) | 4.00 | 4.00 | 4.00 | 5.00 | 5.00 | 3.50 | 3.00 | 5.00 | 4.00 | 4.00 |
| Silica, hydrophilic (e.g. AEROSIL 200) | 2.50 | 2.50 | 2.50 | 1.50 | 1.00 | 1.00 | 2.00 | 1.50 | 2.00 | 1.50 |
| RHEOCIN® stabilizer | 1.00 | 1.50 | 1.00 | 1.50 | 2.00 | 1.00 | 1.00 | 0.50 | — | — |
| Polyvinylpyrrolidone | — | — | — | — | — | — | — | — | 1.00 | 2.00 |
| Favor® T 5056 F | 4.00 | 4.00 | 4.00 | 4.00 | 4.00 | 4.00 | 4.00 | 4.00 | 4.00 | 4.00 |
| Alkylene carbonate propylene carbonate | 1.00 | 1.00 | 1.00 | 1.00 | 1.00 | 1.00 | 1.00 | 1.00 | 1.00 | 1.00 |
| Walnut shell flour (Astopon® fine) | 13.00 | 12.10 | 12.60 | 12.10 | 12.10 | 10.00 | 20.00 | 13.00 | 15.00 | 15.00 |
| Calcium carbonate | — | — | — | — | — | — | 20.00 | | | |
| Kaolin | — | — | — | — | — | — | 27.00 | — | | |
| Titanium dioxide | 1.0 | 1.0 | 1.0 | 1.0 | 1.0 | 1.0 | 1.0 | 1.0 | 1.0 | 1.0 |
| Isooctyl stearate super-oiling agent | 3.90 | 3.90 | 3.90 | 3.90 | 3.90 | 3.90 | 5.00 | 4.00 | 4.00 | 4.00 |
| Total | 100.00 | 100.00 | 100.00 | 100.00 | 100.00 | 100.00 | 100.00 | 100.00 | 100.00 | 100.00 |
| Stability at −4°/20° C./40° C. | stable | stable | stable | stable | stable | stable | stable | stable | stable | stable |
| | 98 | 97 | 98 | 98 | 97 | 95 | 92 | 98 | 95 | 95 |

TABLE 2

| | All recipe examples in wt. %. | | | | | | | | |
|---|---|---|---|---|---|---|---|---|---|
| | 11 | 12 | 13 | 14 | 15 | 16 | 17 | 18 | 19 |
| Carboxylic acid ester of the dimethyl adipate, dimethyl glutarate, dimethyl succinate (DBE) type | 54.60 | 50.50 | 50.50 | 50.50 | 50.50 | 64.60 | 48.00 | — | — |
| Diisobutyl adipate/diisobutyl glutarate/diisobutyl succinate (Rhodiasolv DIB) | — | — | — | — | — | — | — | — | 55.00 |
| (Dimethyl 2-methylglutarate/ dimethyl ethylsuccinate/ dimethyl adipate) Rhodiasolv IRIS | — | — | — | — | — | — | — | 55.00 | — |
| Fatty alcohol ethoxylate (e.g. Rewopal LA6) | 15.00 | 19.50 | 19.50 | 19.50 | 19.50 | 10.00 | 20.00 | 15.00 | 15.00 |
| Stearalkonium bentonite (e.g. TIXOGEL LG-M) | 4.00 | 4.00 | 4.00 | 5.00 | 5.00 | 3.50 | 4.00 | 4.00 | 4.00 |
| Silica, hydrophilic (e.g. AEROSIL 200) | 2.50 | 2.50 | 2.50 | 1.50 | 1.00 | 1.00 | 2.00 | 1.50 | 1.50 |
| RHEOCIN ® stabilizer | 1.00 | 1.50 | 1.00 | 1.50 | 2.00 | 1.00 | — | 1.50 | 1.50 |
| Polyvinylpyrrolidone | — | — | — | — | — | — | 1.00 | | |
| Favor ® T 5056 F | 4.00 | 4.00 | 4.00 | 4.00 | 4.00 | 4.00 | 4.00 | 4.00 | 4.00 |
| Alkylene carbonate propylene carbonate | 1.00 | 1.00 | 1.00 | 1.00 | 1.00 | 1.00 | 1.00 | 1.00 | 1.00 |
| Walnut shell flour (Astopon ® fine) | 13.00 | 12.10 | 12.60 | 12.10 | 12.10 | 10.00 | 15.00 | 13.00 | 13.00 |
| Calcium carbonate | — | — | — | — | — | — | — | — | — |
| Kaolin | — | — | — | — | — | — | — | — | — |
| Titanium dioxide | 1.0 | 1.0 | 1.0 | 1.0 | 1.0 | 1.0 | 1.0 | 1.0 | 1.0 |
| Isooctyl stearate super-oiling agent | 3.90 | 3.90 | 3.90 | 3.90 | 3.90 | 3.90 | 4.00 | 4.00 | 4.00 |
| Total | 100.00 | 100.00 | 100.00 | 100.00 | 100.00 | 100.00 | 100.00 | 100.00 | 100.00 |
| Stability at −4°/20° C./40° C. | stable | stable | stable | stable | stable | stable | stable | stable | stable |

Rhodiasolv DIB (diisobutyl adipate/diisobutyl glutarate/diisobutyl succinate) and Rhodiasolv IRIS (dimetyl 2-methylglutarate/dimethyl ethylsuccinate/dimethyl adipate) are commercial products from Rhodia France, 93306 Aubervilliers Cedex.

TABLE 3

| | All recipe examples in wt. %. | | | | | | | | | |
|---|---|---|---|---|---|---|---|---|---|---|
| | 20 | 21 | 22 | 23 | 24 | 25 | 26 | 27 | 28 | 29 |
| Water | 0 | 0 | 0 | 9.50 | 10.50 | 12.50 | 15.00 | 30.00 | 15.00 | 20.00 |
| Metyl oleate | 52.10 | 52.10 | 52.10 | 45.50 | 44.50 | 42.50 | 40.00 | 24.90 | 34.90 | 36.20 |
| BHT | | | | 0.1 | 0.10 | 0.10 | 0.10 | 0.10 | 0.10 | 0.10 |
| Fatty alcohol ethoxylate (e.g. Marlipal O13/60) | 15.00 | 15.00 | 15.00 | 15.00 | 15.00 | 15.00 | 15.00 | 15.00 | 20.00 | 10.00 |
| Fatty alcohol ether sulfate, 28% | 0 | 0 | 0 | 0 | 0 | 0 | 0 | 0 | 0 | 10.00 |
| Stearalkonium bentonite (e.g. TIXOGEL LG-M) | 3.50 | 3.50 | 3.50 | 3.50 | 3.50 | 3.50 | 3.50 | 3.50 | 3.50 | 3.50 |
| Silica, hydrophilic (e.g. AEROSIL 200) | 2.50 | 2.50 | 2.50 | 2.50 | 2.50 | 2.50 | 2.50 | 2.50 | 2.50 | 2.50 |
| RHEOCIN ® stabilizer | 1.00 | 1.00 | 1.00 | 1.00 | 1.00 | 1.00 | 1.00 | 1.00 | 1.00 | 1.00 |
| CMC (Walocel CRT 2000) | 0 | 0 | 0 | 0 | 0 | 0 | 0 | 0 | 0 | 0.70 |
| Favor ® T 5056 F | 4.00 | 4.00 | 4.00 | 4.00 | 4.00 | 4.00 | 4.00 | 4.00 | 4.00 | 0 |
| Alkylene carbonate e.g. | 1.00 | 1.00 | 1.00 | 1.00 | 1.00 | 1.00 | 1.00 | 1.00 | 1.00 | 0 |

TABLE 3-continued

| | All recipe examples in wt. %. | | | | | | | | | |
|---|---|---|---|---|---|---|---|---|---|---|
| | 20 | 21 | 22 | 23 | 24 | 25 | 26 | 27 | 28 | 29 |
| propylene carbonate | | | | | | | | | | |
| Walnut shell flour | 13.00 | 13.00 | 13.00 | 13.00 | 13.00 | 13.00 | 13.00 | 13.00 | 13.00 | 15.00 |
| Cocamide MEA | 3.00 | 0 | 0 | 0 | 0 | 0 | 0 | 0 | 0 | 0 |
| Cocamide MIPA | 0 | 3.00 | 0 | 0 | 0 | 0 | 0 | 0 | 0 | 0 |
| Cocamide DEA | 0 | 0 | 3.00 | 0 | 0 | 0 | 0 | 0 | 0 | 0 |
| Titanium dioxide | 1.0 | 1.0 | 1.0 | 1.0 | 1.0 | 1.0 | 1.0 | 1.0 | 1.0 | 1.0 |
| Isooctyl stearate super-oiling agent | 3.90 | 3.90 | 3.90 | 3.90 | 3.90 | 3.90 | 3.90 | 4.0 | 4.00 | 0 |
| Total | 100.00 | 100.00 | 100.00 | 100.00 | 100.00 | 100.00 | 100.00 | 100.00 | 100.00 | 100.00 |
| Stability at −4°/20° C./40° C. | stable | stable | stable | stable | unstable | unstable | unstable | unstable | unstable | unstable |
| Cleansing effect in [%] | 98 | 98 | 98 | 90 | 84 | 76 | 66 | 50 | 69 | 63 |

BHT stands for butylhydroxytoluene (2,6-di-tert-butyl-4-methylphenol)
Methyl oleate is a mixture of C16-C18 methyl esters, wherein the C18 methyl ester has a content of >50 wt. %.

Recipe examples 24 to 29 are comparison examples which are not according to the invention. These were unstable and had a significantly poorer cleansing effect than Examples 1 to 23 according to the invention.

The invention claimed is:

1. A skin and hand cleanser comprising:
   a) at least one alkyl ester and/or diester,
   b) >0 to 40 wt. % of at least one surfactant selected from the group consisting of a fatty alcohol ethoxylate, a fatty alcohol ether sulfate and a salt of sulfated and/or sulfonated fatty acid,
   c) 0.5 to 10 wt. % of at least one thixotropy agent that is an organic bentonite that has a maximum loss on ignition at 1,000° C. of 30% by weight and >0.1 wt. % of at least one hydrophilic, pyrogenic silica,
   d) 0 to 30 wt. % of one or more abrasives,
   e) 0 to 5 wt. % of at least one physiologically acceptable carbonic acid ester
   f) 0 to <10 wt. % of water,
   g) optionally one or more viscosity-forming agents,
   h) optionally further cosmetics auxiliary substances, additives and/or active compounds,
   wherein the sum of components a) to h) being 100 wt. %, based on the composition of the cleanser.

2. The skin and hand cleanser of claim 1, comprising as component a) a fatty acid alkyl ester represented by formula (I)

$$R^1CO\text{—}OR^2 \quad (I)$$

in which $R^1CO$ represents a linear or branched, saturated and/or unsaturated acyl radical having 6 to 22 carbon atoms and $R^2$ represents an alkyl radical having 1 to 8 carbon atoms.

3. The skin and hand cleanser of claim 1, comprising as component a) diesters represented by formula (II)

$$R^1OOC\text{—}X\text{—}COOR^2 \quad (II)$$

in which X represents a linear or branched, saturated and/or unsaturated alkyl radical having 0 to 20 carbon atoms and R1 and R2 represents an alkyl radical having 1 to 8 carbon atoms.

4. The skin and hand cleanser of claim 1, comprising 5 to 70 wt. %, based on the total composition, of at least one alkyl ester and/or diester of component a).

5. The skin and hand cleanser of claim 1, comprising as component b) at least one fatty alcohol ethoxylate represented by formula $$R\text{—}O\text{—}(CH2\text{-}CH2\text{-}O)_nH$$

wherein
R=saturated, unsaturated, branched or unbranched alkyl radical and
n=integer from 1 to 11.

6. The skin and hand cleanser of claim 1, comprising 1 to 35 wt. %, based on the total composition, of at least one fatty alcohol ethoxylate as component b).

7. The skin and hand cleanser of claim 1, comprising 5 to 35 wt. %, based on the total composition, of laureth-6 as a fatty alcohol ethoxylate of component b).

8. The skin and hand cleanser of claim 1, comprising at least one fatty alcohol ether sulfate represented by formula $$R\text{—}O\text{—}(CH2\text{-}CH2\text{-}O)_nSO_3X$$

where R=a $C_8$-$C_{18}$ saturated or unsaturated, branched or unbranched alkyl radical,
n=an integer from 1 to 6 and
$X=Na^+$, $NH_4^+$ or $½Mg^{2+}$.

9. The skin and hand cleanser of claim 1, comprising as component c) 0.5 to 7.5 wt. %, based on the total composition, of at least one thixotropy agent and 0.5 wt. % to 5.0 wt. %, based on the total composition, of at least one hydrophilic, pyrogenic silica.

10. The skin and hand cleanser of claim 1, wherein the thixotropy agent of component c) is an organophilic and/or hydrophobic laminar silicate.

11. The skin and hand cleanser of claim 1, wherein the thixotropy agent of the component is a hydrophobic bentonite.

12. The skin and hand cleanser of claim 1, wherein the thixotropy agent of component c) is a stearalkonium bentonite.

13. The skin and hand cleanser of claim 1, comprising 5 to 30 wt. % of one or more abrasives as component d).

14. The skin and hand cleanser of claim 1 that comprises as component d) >0 to 30 wt. % of at least one abrasive selected from the group consisting of sand, pumice flour, calcium carbonate, kaolin, a polyethylene plastic a polyurethane plastic, a natural kernelhusk, a shell flour, an olive kernel, an apricot kernel, a cherry kernel, and maize flour; or mixtures of these.

15. The skin and hand cleanser as claimed in of claim 1 that contains >0 to 30 wt. % of one or more abrasives as component d), wherein the abrasives of component d) are water-swellable solid particles of organic polymers of natural and/or synthetic origin.

16. The skin and hand cleanser of claim 1 that contains >0 to 30 wt. % of one or more abrasives as component d)
   wherein said one or more abrasives are obtained in the form of water-swellable polymers by a process comprising polymerization of the components
   aa) 55 to 99.95 wt. % of monoethylenically unsaturated monomers which carry carboxyl groups,
   bb) 0.05 to 5.0 wt. % of at least one crosslinking agent,
   cc) 0 to 40 wt. % of further monomers which can be copolymerized with a.),
   dd) 0 to 30 wt. % of a water-soluble graft base,
   wherein the constituents aa) to dd) add up to 100 wt. %, and the polymers obtained are optionally post-crosslinked at least once.

17. The skin and hand cleanser of claim 1 that does not contain water.

18. The skin and hand cleanser of claim 1, wherein the at least one thixotropy agent is an organic stearalkonium bentonite that has a maximum loss on ignition at 1,000° C. of 29% by weight; and which is free of water.

19. A composition comprising:
   a) at least one alkyl ester and/or diester,
   b) >0 to 40 wt. % of at least one surfactant selected from the group consisting of a fatty alcohol ethoxylate, a fatty alcohol ether sulfate and a salt of sulfated and/or sulfonated fatty acid,
   c) 0.5 to 10 wt. % of at least one thixotropy agent that is an organophilic and/or hydrophobic laminar silicate and >0.1 wt. % of at least one hydrophilic, pyrogenic silica,
   d) 0 to 30 wt. % of one or more abrasives,
   e) 0 to 5 wt. % of at least one physiologically acceptable carbonic acid ester, and
   f) 0 to <10 wt. % of water.

20. The composition of claim 19 that contains >0 to 40 wt. % of at least one fatty alcohol ethoxylate.

21. The composition of claim 19, wherein the at least one thixotropy agent is an organic bentonite that has a maximum loss on ignition at 1,000° C. of 30% by weight; and which is free of water.

* * * * *